United States Patent [19]  [11] Patent Number: 4,551,448
Seufert et al.  [45] Date of Patent: Nov. 5, 1985

[54] FLUOROETHOXYPHENYL (DI)THIOPHOSPHATES, A PROCESS FOR THEIR PREPARATION AND THEIR USE FOR CONTROLLING PESTS

[75] Inventors: Walter Seufert, Speyer; Juergen Varwig, Heidelberg; Gerd Husslein, Ludwigshafen; Wolfgang Seppelt, Bobenheim-Roxheim; Heinrich Adolphi, Limburgerhof, all of Fed. Rep. of Germany

[73] Assignee: BASF Aktiengesellschaft, Fed. Rep. of Germany

[21] Appl. No.: 482,775

[22] Filed: Apr. 7, 1983

[30] Foreign Application Priority Data

Apr. 8, 1982 [DE] Fed. Rep. of Germany ....... 3213152
Jul. 8, 1982 [DE] Fed. Rep. of Germany ....... 3225507

[51] Int. Cl.$^4$ .................... A01N 57/14; C07F 9/165
[52] U.S. Cl. .................................. 514/130; 260/951; 260/950; 260/940
[58] Field of Search ............... 260/951, 950; 424/217; 514/130

[56] References Cited

U.S. PATENT DOCUMENTS 3,755,511 8/1973 McKendry et al. ............... 260/951
3,825,636 7/1974 Kishino et al. ...................... 260/951
3,933,947 1/1976 Kishino et al. ...................... 260/951
4,139,615 2/1979 Hoffman et al. ................... 424/216

FOREIGN PATENT DOCUMENTS 0056149 6/1982 European Pat. Off. .

Primary Examiner—Anton H. Sutto
Attorney, Agent, or Firm—Keil & Weinkauf

[57] ABSTRACT

Fluoroethoxyphenyl (di)thiophosphates of the formula

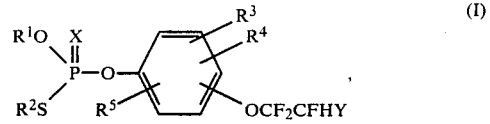

where $R^1$ is alkyl of 1 to 3 carbon atoms, $R^2$ is alkyl of 1 to 5 carbon atoms, alkoxyalkyl or alkylthioalkyl, each of 2 to 8 carbon atoms, or cycloalkyl of 3 to 6 carbon atoms, $R^3$, $R^4$ and $R^5$ independently of one another are each hydrogen, fluorine, chlorine, bromine or cyano, or alkyl of 1 to 4 carbon atoms which is unsubstituted or substituted by halogen, cyano, alkoxy or alkylthio, X is oxygen or sulfur, and Y is hydrogen, fluorine, chlorine or bromine, their preparation and their use as pesticides.

4 Claims, No Drawings

FLUOROETHOXYPHENYL (DI)THIOPHOSPHATES, A PROCESS FOR THEIR PREPARATION AND THEIR USE FOR CONTROLLING PESTS

The present invention relates to fluoroethoxyphenyl(di)thiophosphates, a process for their preparation and pesticides containing these compounds as active ingredients.

U.S. Pat. No. 3,755,511 discloses that O,O-dialkyl O-(fluoroethoxyphenyl)(thiono)phosphates can be used as fungicidal, herbicidal and insecticidal agents.

We have found that fluoroethoxyphenyl(di)thiophosphates of the formula

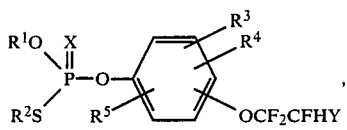
(I)

where $R^1$ is alkyl of 1 to 3 carbon atoms, $R^2$ is alkyl of 1 to 5 carbon atoms, alkoxyalkyl or alkylthioalkyl, each of 2 to 8 carbon atoms, or cycloalkyl of 3 to 6 carbon atoms, $R^3$, $R^4$ and $R^5$ independently of one another are each hydrogen, fluorine, chlorine, bromine or cyano, or alkyl of 1 to 4 carbon atoms which is unsubstituted or substituted by halogen, cyano, alkoxy or alkylthio, X is oxygen or sulfur, and Y is hydrogen or halogen (F, Cl or Br), effectively control pests from the classes of insects, arachnida and nematodes. The action of these compounds is far superior to that of the known O,O-dialkyl O-(fluoroethoxyphenyl)(thiono)phosphates of similar structure.

In formula I, $R^1$ is alkyl of 1 to 3 carbon atoms, eg. methyl, ethyl, n-propyl or i-propyl, $R^2$ is alkyl of 1 to 5 carbon atoms, eg. methyl, ethyl, n-propyl, i-propyl, n-butyl, sec.-butyl, i-butyl, n-pentyl, 1-methyl-n-butyl or 3-methyl-n-pentyl, alkoxyalkyl or alkylthioalkyl, each of 2 to 8, preferably 2 to 5, carbon atoms, eg. 2-methoxyethyl, 2-ethoxyethyl, 2-isopropoxyethyl, 2-methylthioethyl or 2-ethylthioethyl, or cycloalkyl of 3 to 6 carbon atoms, eg. cyclopentyl or cyclohexyl, and $R^3$, $R^4$ and $R^5$ can be identical or different and are each hydrogen, halogen, eg. chlorine, bromine or fluorine, alkyl of 1 to 4, preferably 1 or 2, carbon atoms, eg. methyl, ethyl, n-propyl or tert.-butyl, which in turn can be substituted by halogen, in particular fluorine or chlorine, cyano, or alkoxy or alkylthio, each of 1 to 4 carbon atoms, eg. methoxy, methylthio, ethoxy or ethylthio.

The fluoroethoxy group can be in the 2-, 3- or 4-position with respect to the phosphoric acid radical, and is preferably in the 2-position and in particular in the 4-position.

The fluoroethoxyphenyl(di)thiophosphates of the formula I are obtained by a process wherein an O,S-dialkylphosphoric acid chloride of the formula

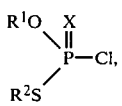
(II)

where $R^1$, $R^2$ and X have the above meanings, is reacted with a fluoroethoxyphenol of the formula

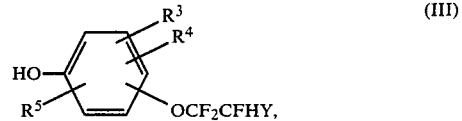
(III)

where $R^3$, $R^4$, $R^5$ and Y have the above meanings, in the presence or absence of an acid acceptor and in the presence or absence of a diluent, or with a salt of a fluoroethoxyphenol of the formula III, in the presence or absence of a diluent.

The course of the reaction can be represented by the following equation:

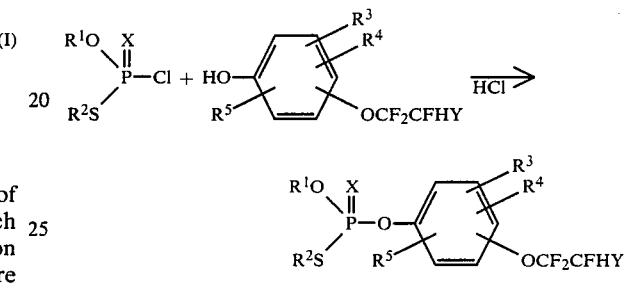

The reaction of a phosphoric acid ester chloride of the formula II with a phenol of the formula III can be carried out in an organic diluent, eg. acetone, acetonitrile, benzene, toluene, chlorobenzene or methyl ethyl ketone, or in a two-phase system, eg. toluene/water or dichloromethane/water.

Advantageously, from 1 to 2 moles of an acid acceptor are added per mole of phenol of the formula III; preferably, an excess of about 10% is used. Suitable acid acceptors are bases, such as alkali metal carbonates, eg. potassium carbonate, alkali metal hydroxides, eg. sodium hydroxide, or tertiary amines, eg. triethylamine. Instead of a base and phenol, it is also possible to react a salt of the phenol with the phosphoric acid ester chloride. Suitable salts are alkali metal salts, alkaline earth metal salts or unsubstituted or substituted ammonium salts, such as alkylammonium salts, eg. dimethylammonium or triethylammonium salts, sodium salts and calcium salts.

The reaction takes place in general at below 100° C., preferably from 20° to 70° C., in general under atmospheric pressure.

To carry out the process, the starting materials are employed in principle in stoichiometric amounts, although an excess of one or other of the reactants can be advantageous in some cases. Advantageously, from 0.9 to 1.1 moles of phosphoric acid ester chloride are employed per mole of phenol.

The reaction mixture is worked up in a conventional manner, for example by adding water and separating the phases. The crude product can be purified by distillation or column chromatography.

O,S-Dialkylphosphoric acid chlorides of the formula II are known, and can be prepared by a conventional process (German Laid-Open Application DOS No. 2,642,982; and J. Org. Chem. 30 (1965), 3217).

Some of the fluoroethoxyphenols of the formula III are known (German Laid-Open Application DOS No. 2,312,906); those which are not known can be obtained from the corresponding anilines by diazotization and boiling down (Houben-Weyl, Volume 6/1 c (1976), page 247). Such anilines in turn have been disclosed in, for example, Z. Naturforsch. 28 c (1973), 653, and Bull-.Soc.Chim., 5th series (1957), 581.

The halogenation of the phenols can likewise be carried out by a conventional process (European Pat. No. 22,954).

Compounds according to the invention can also be obtained by further processes outlined below:

Fluoroethoxyphenyl thiophosphates of the formula Ia can be prepared by an Arbusow reaction, in which a phosphite of the formula IV is reacted with a sulfenyl chloride of the formula $R^2SCl$, in accordance with the following equation:

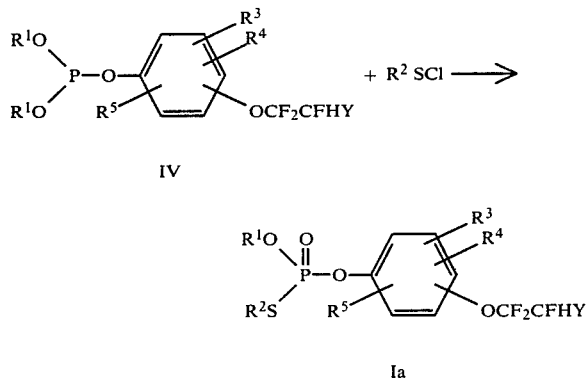

Fluoroethoxyphenyl thiophosphates of the formula Ia can also be obtained by alkylating a phosphoric acid ester salt of the formula V with an alkylating agent of the formula $R^2Z$:

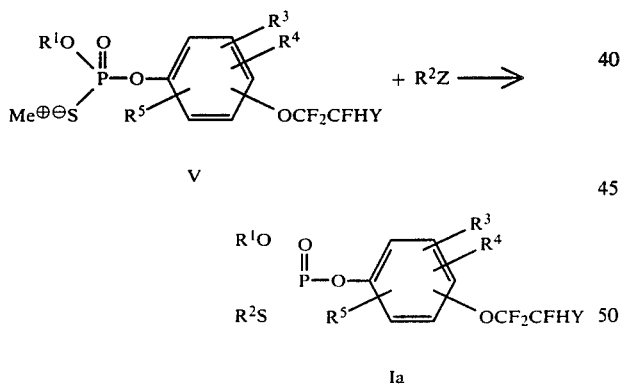

Furthermore, compounds of the formula I can be obtained by reacting a phosphoric acid ester dichloride of the formula VI with an alcohol of the formula $R^1OH$ and then reacting the product with a mercaptan of the formula $R^2SH$:

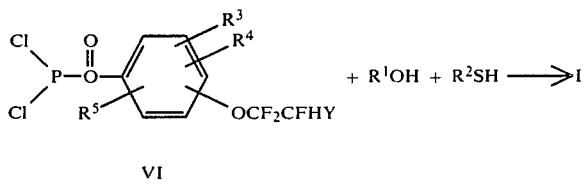

In these equations, $R^1$, $R^2$, $R^3$, $R^4$, $R^5$ and X have the above meanings, Me⊕ is a metal cation or an unsubstituted or alkyl-substituted ammonium ion, and Y is halide, eg. iodide, bromide or chloride, or alkylsulfate, eg. methylsulfate. The choice of a preparation process from those stated above is made in general on the basis of economic considerations.

(a) Preparation of 4-(2-bromo-1,1,2-trifluoroethoxy)-nitrobenzene 278 g of 4-nitrophenol and 56 g of potassium hydroxide were dissolved in 800 ml of dimethylformamide, 179 g of bromotrifluoroethylene were fed in, a little at a time, at 40° C., and stirring was then continued for 2 hours at 60° C. The solvent was removed under reduced pressure in a rotary evaporator, the residue was poured into ice-water and extracted with 3×500 ml of methylene chloride, the extract was washed with dilute sodium hydroxide solution and water and dried over Na₂SO₄, and the solvent was removed. When the residue was distilled, 279.5 g of pure product passed over at 114° C./1.3 mbar.

(b) Preparation of 4-(2-chloro-1,1,2-trifluoroethoxy)-nitrobenzene

The procedure described above is followed, using a corresponding amount of chlorotrifluoroethylene. 327 g (64% yield) of the compound (boiling point 80° C./0.3 mbar) were obtained.

(c) 4-(2-Bromo-1,1,2-trifluoroethoxy)-aniline 700 ml of absolute ethyl acetate were added to 275 g of 4-(2-bromo-1,1,2-trifluoroethoxy)-nitrobenzene, and hydrogenation was carried out using 20 g of palladium on active carbon. The catalyst was filtered off and the solvent was removed. 251 g of the compound were obtained; this was pure according to NMR analysis.

The following compounds were prepared by a similar procedure:

| | bp. 81° C./0.2 mbar | 73% yield |
|---|---|---|
| NH₂—⌬—OCF₂CF₂H | | |
| ⌬—OCF₂—CF₂H  \| NH₂ | directly reacted further | 98% yield |
| NH₂—⌬—O—CF₂—CFHCl | bp. 130° C./6 mbar | 86% yield |
| ⌬—OCF₂CFHCl  \| NH₂ | bp. 86° C./0.1 mbar | 76% yield |

(d) 4-(2-Bromo-1,1,2-trifluoroethoxy)-phenol 40 g of 4-(2-bromo-1,1,2-trifluoroethoxy)-aniline were added dropwise, at 10° C., to 400 ml of 2.5N sulfuric acid, after which 11 g of sodium nitrite in 30 ml of water were added dropwise at 0° C., and the mixture was stirred for a further hour at 10° C.

Steam distillation of 100 g of CuSO₄ and 33 g of urea in 500 ml of water was begun, and the solution containing sulfuric acid was added a little at a time. Distillation was continued for not more than 15 minutes after completion of the dropwise addition. The cold distillate was then extracted by shaking with methylene chloride, the methylene chloride solution was washed once with ice water and dried over sodium sulfate, the solvent was removed and the residue was distilled at 86° C./0.15 mbar. 22 g of the phenol were obtained.

In the same manner, the anilines described above were converted to the phenols listed below:

| | Bp. | Yield |
|---|---|---|
| 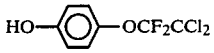 HO—⟨○⟩—OCF$_2$CCl$_2$ | 80° C./0.15 mbar | 70% |
| 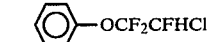 ⟨○⟩—OCF$_2$CFHCl  HO | 87° C./0.3 mbar | 60% |
| HO—⟨○⟩—CCF$_2$—CF$_2$H | 80° C./1.5 mbar | 60% |
| ⟨○⟩—OCF$_2$—CF$_2$H  OH | 55° C./0.6 mbar | 43% |
| HO—⟨○⟩—OCF$_2$—CFClH | 69° C./0.15 mbar | 79% |

(e) 2-Chloro-4-(2-bromo-1,1,2-trifluoroethoxy)-phenol 12.2 g of 4-(2-bromo-1,1,2-trifluoroethoxy)-phenol and 5 drops of diphenyl sulfide were dissolved in 30 ml of glacial acetic acid, and 6.1 g of sulfuryl chloride were added, a little at a time, at 25° C. After 3 hours at 25° C., the volatile components were removed, the residue was taken up with 300 ml of methylene chloride, and the solution was washed with 100 ml of 10% strength NaHCO$_3$ solution and 100 ml of water, dried over Na$_2$SO$_4$ and distilled at 82° C./0.3 mbar. Yield: 12.6 g.

The following compounds were prepared by a similar procedure:

| | Bp. | Yield |
|---|---|---|
| 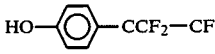 HO—⟨○⟩—OCF$_2$CF$_2$H  Cl | 50° C./0.4 mbar | 93% |
| HO—⟨○⟩—OCF$_2$—CF$_2$ClH  Cl | 55° C./0.15 mbar | 84% |

(f) 2-Bromo-4-(2-bromo-1,1,2-trifluoroethoxy)-phenol 7.2 g of bromine in 30 ml of chloroform were added dropwise, at 25° C., to a solution of 12.2 g of 4-(2-bromo-1,1,2-trifluoroethoxy)-phenol in 100 ml of anhydrous chloroform, and the mixture was stirred for 12 hours at 25° C. The solvent was removed, and the residue was distilled at 100° C./0.4 mbar to give 15.5 g of pure product.

The following compounds were obtained by a similar procedure:

| | Bp. | Yield |
|---|---|---|
| 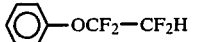 HO—⟨○⟩—OCF$_2$—CF$_2$H  Br | 45° C./0.15 mbar | 97% |
| Br—⟨○⟩—OCF$_2$—CF$_2$H  OH | 51° C./0.15 mbar | 90% |
| HO—⟨○⟩—O—CF$_2$—CFHCl  Br | 80° C./0.6 mbar | 95% |

EXAMPLE 1

O-Ethyl S-propyl O-[4-(1,1,2,2-tetrafluoroethoxy)-phenyl]monothiophosphate 6.1 g of O-ethyl S-propylthiophosphoric acid chloride were added dropwise to 6.3 g of 4-(1,1,2,2-tetrafluoroethoxy)-phenol and 6.9 g of potassium carbonate in 100 ml of acetonitrile, and the mixture was stirred for 14 hours at 50° C. and thereafter for 12 hours at room temperature.

Thereafter, the solvent was removed in a rotary evaporator, 400 ml of toluene and 100 ml of water were added to the residue, and the phases were separated, the organic phase was washed with 2N sodium hydroxide solution and then with water, and dried with sodium sulfate, and the solvent and volatile impurities were removed at 40° C. under a reduced pressure of 0.1 mbar. 8.1 g of product of refractive index $n_D^{23} = 1.4671$ were obtained as the residue.

EXAMPLE 2

O-Ethyl S-propyl-O-[2-bromo-4-(2-bromo-1,1,2-trifluoroethoxy)-phenyl]monothiophosphate 4.0 g of O-ethyl-S-propylthiophosphoric acid chloride were added dropwise to 6.9 g of 2-bromo-4-(2-bromo-1,1,2-trifluoroethoxy)-phenol and 6.9 g of potassium carbonate in 100 ml of acetonitrile, and the mixture was stirred for 4 hours at 50° C. and thereafter for 12 hours at room temperature.

Thereafter, the solvent was removed in a rotary evaporator, 400 ml of toluene and 100 ml of water were added to the residue, the phases were separated, the organic phase was washed with 2N sodium hydroxide solution and then with water, and dried with sodium sulfate, and the solvent and volatile impurities were removed under reduced pressure. 7.0 g of product of refractive index $n_D^{21} = 1.5154$ were obtained as the residue.

EXAMPLE 3

O-Ethyl S-propyl-O-[2-chloro-4-(2-bromo-1,1,2-trifluoroethoxy)-phenyl]monothiophosphate 3.2 g of O-ethyl-S-propylthiophosphoric acid chloride were added dropwise to 4.9 g of 2-chloro-4-(2-bromo-1,1,2-trifluoroethoxy)-phenol and 6.9 g of potassium carbonate in 100 ml of acetonitrile, and the mixture was stirred for 4 hours at 50° C. and thereafter for 12 hours at room temperature.

Thereafter, the solvent was removed in a rotary evaporator, 400 ml of toluene and 100 ml of water were added to the residue, the phases were separated, the organic phase was washed with 2N sodium hydroxide solution and then with water, and dried with sodium sulfate, and the solvent and volatile impurities were removed under reduced pressure. 6.0 g of product of refractive index $n_D^{21} = 1.5044$ were obtained as the residue.

By using other starting materials or intermediates and following a procedure similar to that described above, the substances listed in Table 1 below were obtained.

TABLE 1

| No. | Y CFH—CH$_2$O— | R$^3$R$^4$R$^5$ | X | SR$^2$ | n$_D$ |
|---|---|---|---|---|---|
| 1 | 4-CF$_2$H—CF$_2$O— | H | O | 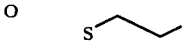 | $n_D^{23}$ 1.4671 |
| 2 | " | " | O | 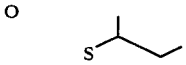 | $n_D^{23}$ 1.4671 |
| 3 | " | " | O | 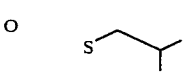 | $n_D^{21}$ 1.4677 |
| 4 | " | " | O |  | $n_D^{24}$ 1.4663 |
| 5 | " | " | S |  | $n_D^{21}$ 1.4980 |
| 6 | " | " | S |  | $n_D^{24}$ 1.4955 |
| 7 | " | " | S | 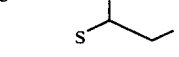 | $n_D^{24}$ 1.4921 |
| 8 | " | 2-Cl | O | 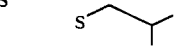 | $n_D^{20}$ 1.4791 |
| 9 | " | " | O | 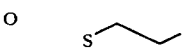 | $n_D^{20}$ 1.4804 |
| 10 | " | " | O |  | $n_D^{20}$ 1.4778 |
| 11 | " | " | S | 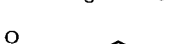 | $n_D^{20}$ 1.5028 |
| 12 | " | " | S |  | $n_D^{20}$ 1.5059 |
| 13 | " | 2-Br | O | 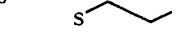 | $n_D^{21}$ 1.4898 |
| 14 | " | " | O | 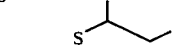 | $n_D^{21}$ 1.4887 |
| 15 | " | " | O | 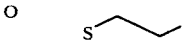 | $n_D^{20}$ 1.4879 |
| 16 | " | " | S | 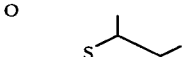 | $n_D^{22}$ 1.5135 |
| 17 | " | " | S |  | $n_D^{22}$ 1.5170 |
| 18 | 2 CF$_2$H—CF$_2$O— | H | O |  | $n_D^{20}$ 1.4702 |
| 19 | " | " | O | 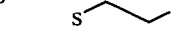 | $n_D^{21}$ 1.4670 |
| 20 | " | " | O | 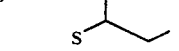 | $n_D^{21}$ 1.4662 |

TABLE 1-continued

| No. | Y CFH—CH$_2$O— | R$^3$R$^4$R$^5$ | X | SR$^2$ | n$_D$ |
|---|---|---|---|---|---|
| 21 | " | 4-Br or 6-Br | O | S-CH$_2$CH$_2$CH$_3$ | n$_D^{23}$ 1.4885 |
| 22 | " | " | O | S-CH(CH$_3$)CH$_3$ | n$_D^{23}$ 1.4868 |
| 23 | 4-ClCFH—CF$_2$O— | H | O | S-CH$_2$CH$_2$CH$_3$ | n$_D^{20}$ 1.4851 |
| 24 | " | " | O | S-CH(CH$_3$)CH$_3$ | n$_D^{22}$ 1.4838 |
| 25 | " | " | O | S-CH$_2$CH(CH$_3$)$_2$ | n$_D^{22}$ 1.4832 |
| 26 | " | " | O | S-CH$_2$CH$_2$OCH$_2$CH$_3$ | n$_D^{22}$ 1.4822 |
| 27 | " | " | S | S-CH$_2$CH$_2$CH$_3$ | n$_D^{22}$ 1.5080 |
| 28 | " | " | S | S-CH(CH$_3$)CH$_3$ | n$_D^{25}$ 1.5090 |
| 29 | " | " | S | S-CH$_2$CH(CH$_3$)$_2$ | n$_D^{22}$ 1.5080 |
| 30 | " | 2-Cl | O | S-CH$_2$CH$_2$CH$_3$ | n$_D^{22}$ 1.4933 |
| 31 | " | " | O | S-CH(CH$_3$)CH$_3$ | n$_D^{24}$ 1.4923 |
| 32 | " | " | O | S-CH$_2$CH(CH$_3$)$_2$ | n$_D^{25}$ 1.4877 |
| 33 | " | " | O | S-CH$_2$CH$_2$OCH$_2$CH$_3$ | n$_D^{25}$ 1.4898 |
| 34 | " | " | S | S-CH$_2$CH$_2$CH$_3$ | n$_D^{25}$ 1.5151 |
| 35 | " | " | S | S-CH(CH$_3$)CH$_3$ | n$_D^{25}$ 1.5171 |
| 36 | " | " | S | S-CH$_2$CH(CH$_3$)$_2$ | n$_D^{22}$ 1.5162 |
| 37 | " | 2-Br | O | S-CH$_2$CH$_2$CH$_3$ | n$_D^{22}$ 1.5042 |
| 38 | " | " | O | S-CH(CH$_3$)CH$_3$ | n$_D^{22}$ 1.5043 |
| 39 | " | " | O | S-CH$_2$CH(CH$_3$)$_2$ | n$_D^{22}$ 1.5022 |
| 40 | " | " | O | S-CH$_2$CH$_2$OCH$_2$CH$_3$ | n$_D^{26}$ 1.4991 |
| 41 | " | " | S | S-CH$_2$CH$_2$CH$_3$ | n$_D^{26}$ 1.5260 |
| 42 | " | " | S | S-CH(CH$_3$)CH$_3$ | n$_D^{25}$ 1.5282 |

TABLE 1-continued

| No. | Y CFH—CH₂O— | R³R⁴R⁵ | X | SR² | $n_D$ |
|---|---|---|---|---|---|
| 43 | " | " | S |  | $n_D^{26}$ 1.5258 |
| 44 | 4-BrCFH—CF₂O— | H | O |  | $n_D^{23}$ 1.4951 |
| 45 | " | " | O |  | $n_D^{23}$ 1.4941 |
| 46 | " | " | O |  | $n_D^{23}$ 1.4919 |
| 47 | " | " | S |  | $n_D^{23}$ 1.5171 |
| 48 | " | 2-Cl | O |  | $n_D^{21}$ 1.5044 |
| 49 | " | " | O |  | $n_D^{21}$ 1.5019 |
| 50 | " | 2-Br | O |  | $n_D^{21}$ 1.5154 |
| 51 | " | " | O |  | $n_D^{21}$ 1.5126 |
| 52 | 3-ClCFH—CF₂O— | H | O |  | $n_D^{22}$ 1.4840 |
| 53 | " | H | O |  | $n_D^{22}$ 1.4812 |
| 54 | " | 4-Cl or 6-Cl | O |  | $n_D^{23}$ 1.4907 |
| 55 | " | " | O |  | $n_D^{21}$ 1.4902 |

Examples of further compounds which may be obtained by the process described above are given in Table 2.

TABLE 2

| YCFH—CF₂O— | R³R⁴R⁵ | X | SR² | OR¹ |
|---|---|---|---|---|
| 4-CF₂H—CF₂—O— | H | O |  | OCH₃ |
| " | 2-Cl | O |  | " |
| " | " | O |  | " |
| " | 2-Br | O |  | " |
| " | " | O |  | " |
| " | 2,6-Cl₂ | O |  | OC₂H₅ |
| " | " | O |  | " |
| " | 2,6-Br | O |  | " |

TABLE 2-continued

| YCFH—CF₂O— | R³R⁴R⁵ | X | SR² | OR¹ |
|---|---|---|---|---|
| " | " | O |  | " |
| 3-CF₂HCF₂O— | H | O |  | " |
| " | " | O |  | " |
| " | " | O |  | " |
| " | " | S |  | " |
| " | 4-Cl | O |  | " |
| " | " | O |  | " |
| " | 6-Cl | O |  | " |

TABLE 2-continued

| YCFH—CF₂O— | R³R⁴R⁵ | X | SR² | OR¹ |
|---|---|---|---|---|
| " | " | O | SCH(CH₃)C₂H₅ | " |
| " | 4-Br | O | SC₃H₇-n | " |
| " | " | O | SCH(CH₃)₂ | " |
| " | 6-Br | O | SC₃H₇-n | " |
| " | " | O | SCH(CH₃)C₂H₅ | " |
| 2-CF₂HCF₂O— | 4-Br | O | SCH(CH₃)C₂H₅ | " |
| " | " | S | SC₃H₇-n | " |
| " | 4-Cl | O | SC₃H₇-n | " |
| " | " | O | SCH(CH₃)C₂H₅ | " |
| " | " | O | SCH(CH₃)C₂H₅ | " |
| " | " | S | SC₃H₇-n | " |
| " | 6-Cl | O | SC₃H₇-n | " |
| " | " | O | SCH(CH₃)C₂H₅ | " |
| " | " | O | SCH(CH₃)C₂H₅ | " |
| " | " | O | SC₃H₇-n | " |
| " | 4,6-Cl₂ | O | SC₃H₇-n | " |
| " | " | O | SCH(CH₃)₂ | " |
| 4-CFClHCF₂O— | " | O | SC₃H₇-n | " |
| " | " | O | SCH(CH₃)C₂H₅ | " |
| " | " | O | SCH(CH₃)C₂H₅ | " |
| " | " | S | SC₃H₇-n | " |
| " | 4,6-Br₂ | O | SC₃H₇-n | " |
| " | " | O | SCH(CH₃)C₂H₅ | " |
| 3-CFClHCF₂O— | 4-Br | O | SC₃H₇-n | " |
| " | " | O | SCH(CH₃)C₂H₅ | " |
| " | 6-Br | O | SC₃H₇-n | " |
| " | " | O | SCH(CH₃)C₂H₅ | " |
| 2-CFClHCF₂O— | H | O | SC₃H₇-n | " |
| " | H | O | SCH(CH₃)C₂H₅ | " |
| " | H | O | SCH(CH₃)₂ | " |
| " | H | S | SC₃H₇-n | " |
| " | 4-Cl | O | SC₃H₇-n | " |
| " | " | O | SCH(CH₃)C₂H₅ | " |
| " | " | O | SC₃H₇-n | " |
| " | " | O | SCH(CH₃)C₂H₅ | " |
| " | 4-Br | O | SC₃H₇-n | " |
| " | " | O | SCH(CH₃)C₂H₅ | " |
| " | " | O | SCH(CH₃)C₂H₅ | " |
| " | " | S | SC₃H₇-n | " |
| " | 4,6-Cl₂ | O | SCH(CH₃)C₂H₅ | " |
| " | 4,6-Br₂ | O | SC₃H₇-n | " |
| 3-CFBrHCF₂O— | H | O | SC₃H₇-n | " |
| " | H | O | SCH(CH₃)C₂H₅ | " |
| " | H | O | SC₃H₇-n | " |
| " | 4-Cl | O | SCH(CH₃)C₂H₅ | " |

TABLE 2-continued

| YCFH—CF$_2$O— | R$^3$R$^4$R$^5$ | X | SR$^2$ | OR$^1$ |
|---|---|---|---|---|
| " | 6-Cl | O | S–CH$_2$CH$_2$CH$_3$ | " |
| " | 4-Br | O | S–CH$_2$CH$_2$CH$_3$ | " |
| " | 6-Br | O | S–CH$_2$CH$_2$CH$_3$ | " |
| 2-CFBrHCF$_2$O— | H | O | S–CH$_2$CH$_2$CH$_3$ | " |
| " | H | O | S–CH(CH$_3$)$_2$ | " |
| " | H | O | S–CH$_2$CH(CH$_3$)– | " |
| " | H | S | S–CH$_2$CH$_2$CH$_3$ | " |
| " | 4-Cl | O | S–CH$_2$CH$_2$CH$_3$ | " |
| " | " | O | S–CH(CH$_3$)$_2$ | " |
| " | " | O | S–CH$_2$CH(CH$_3$)– | " |
| " | " | S | S–CH$_2$CH$_2$CH$_3$ | " |
| " | 4-Br | O | S–CH$_2$CH$_2$CH$_3$ | " |
| " | " | O | S–CH(CH$_3$)$_2$ | " |
| " | " | O | S–CH$_2$CH(CH$_3$)– | " |
| " | " | S | S–CH$_2$CH$_2$CH$_3$ | " |
| " | 6-Cl | O | S–CH$_2$CH$_2$CH$_3$ | " |
| " | " | O | S–CH(CH$_3$)$_2$ | " |

To compare the biological action of the active ingredients according to the invention with that of a prior art agent, the compound

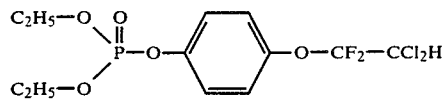

disclosed in Example 3 of U.S. Pat. No. 3,755,511 was included in the experiments.

Contact action on oriental cockroaches (Blatta orientalis)

The bottom of 1 liter preserving jars was lined with acetonic solutions of the active ingredients. After the solvent had evaporated, 5 adult cockroaches were introduced into each jar. The kill rate was determined after 48 hours.

In this test, the active ingredients of Example Nos. 1, 2, 4, 8, 9, 10, 13, 14, 15, 18, 19, 20, 21, 22, 23, 24, 25, 30, 44, 53 and 54, at a rate of from 0.02 to 0.1 mg, achieved complete kill, whereas the comparative agent, at a rate of 1 mg, killed less than 50% of the animals.

Contact action on mosquito larvae (Aedes aegypti)

Formulations of the active ingredients were added to 200 ml of tapwater; 30 to 40 mosquito larvae of the 4th larval stage were then introduced. The temperature was kept at 22° C. The action was assessed after 24 hours.

The compounds of Example Nos. 8, 9, 13, 14, 15, 21, 22, 28, 31, 34, 35, 37, 42, 43, 45, 47, 48, 49, 50, 51 and 54 had, at concentrations of from 0.0002 to 0.01 ppm (depending on the compound), a 100% action, whereas the comparative agent, at a concentration at least 100 times stronger, achieved only a 50% action.

Breeding experiment with housefly larvae (Musca domestica)

4.5 ml of skimmed milk was introduced into 50 ml penicillin flasks, and 0.5 ml of aqueous active ingredient formulations was added. After brief mixing, a ball of cottonwool (from Hartmann, Maintal) was introduced and about 50 egg larvae of the housefly were placed on it. The flasks were covered, and stored at room temperature for 7 days.

In Example Nos. 1, 2, 3, 5, 6, 7, 8, 10, 11, 12, 13, 14, 15, 18, 19, 20, 21, 22, 31, 32, 33, 34, 35, 37, 38, 39, 40, 41, 42, 43, 45, 46, 47, 48, 49, 50, 51, 52, 53 and 54, the concentration for achieving 100% kill was from 0.2 to 2 ppm. The comparative agent was still ineffective at 20 ppm.

Contact action on cotton stainers (Dysdercus intermedius)

Petri dishes 10 cm in diameter were lined with 1 ml of acetonic solutions of the active ingredients. After the solvent had evaporated, 20 larvae of the penultimate stage were placed in the dishes, and the effect was registered after 24 hours.

The compounds of Example Nos. 1, 2, 3, 4, 8, 9, 10, 13, 19, 52 and 53 had a 100% action at from 0.002 to 0.01 mg; by contrast, the comparative agent only had an absolute action at 0.2 mg.

Contact action and effect of ingested food on caterpillars of the diamondback moth (Plutella maculipennis)

Leaves of young cabbage plants were dipped for 3 seconds in aqueous emulsions of the active ingredients, and, after briefly having allowed excess liquid to drip off, were placed on a moist filter paper in a Petri dish. 10 caterpillars of the 4th stage were then placed on the leaves. The action was assessed after 48 hours.

For the compounds of Example Nos. 1, 2, 3, 4, 5, 6, 8, 10, 12, 13, 14, 15, 18, 19, 20, 21, 22, 24, 26, 30, 33, 37, 45, 46, 47, 48, 49, 52, 53 and 54, the kill rate was between about 80 and 100% at application concentrations of 0.0004 to 0.002%; the comparative agent had an 80% action at 0.04%.

Contact action on bean aphids (*Aphis fabae*); spray experiment

Potted bean plants (*Vicia faba*) with extensive bean aphid colonies were sprayed to runoff in a spray booth with aqueous formulations of the active ingredients. Assessment took place after 24 hours.

The compounds of Example Nos. 1, 2, 3, 4, 8, 9, 10, 12, 14, 15, 17, 18, 19, 20, 21, 22, 23, 24, 25, 30, 32, 33 and 45 had a 100% action at a concentration of 0.004 to 0.02%; the comparative agent was only partially effective at 0.1%.

Systemic action on caterpillars (*Prodenia litura*)

200 ml of quartz sand was filled into 250 ml polystyrene beakers, which were then placed in 8-vessel pallets. 5 Indian corn grains were introduced into each beaker (about 1 cm beneath the surface). Each beaker was then moistened with 50 ml of water and covered with a fitting transparent plastic hood. After 8 days, the hoods were removed and treatment was effected after 10 days. Each beaker was watered with 40 ml of the aqueous active ingredient formulations, and, after a further day, 50 ml of dry quartz sand was added as a cover to each beaker. The purpose of this sand cover is to prevent the test animals from coming into contact with the treated surface.

Plastic cylinders 7 cm in diameter were placed on each beaker, 5 caterpillars in the 3rd larval stage were introduced, and the cylinders were capped with a wire gauze cover.

Solutions of active ingredients from Example Nos. 1, 3, 4, 5, 8, 10, 13, 18, 19, 20, 22, 30 and 52 were generally fully effective at 0.004 to 0.02% of active ingredient, whereas the comparative agent was still ineffective at 0.1% (no systemic action at a technically reasonable application rate).

Action on spider mites (*Tetranychus telarius*) A

Potted bush beans which had developed the first pair of true leaves and were under heavy attack from spider mites (*Tetranychus telarius*) of all stages were sprayed to runoff from all sides in a spray cabinet with aqueous formulations of the active ingredients.

The plants were placed on a rotatable disc and were sprayed with 50 ml of spray liquor. Spraying lasted for about 22 seconds. The plants were investigated after 8 days for living spider mites.

The compounds of Example Nos. 1, 2, 3, 5, 13, 14, 21, 23, 24, 25, 26, 27, 29, 30, 31, 32, 33, 34, 37, 38, 39, 40, 44, 45, 46, 48, 49, 50, 51, 52, 53 and 54 had a 100% action at concentrations of 0.002 to 0.01%, whereas the comparative agent had only a poor action at 0.1%.

Action on spider mites (*Tetranychus telarius*) B

Potted bush beans which had developed the second pair of true leaves were sprayed to runoff from all sides in a spray cabinet with aqueous formulations of the active ingredients.

The plants were placed on a rotatable disc and were sprayed with 50 ml of spray liquor. Spraying lasted for about 22 seconds. After 24 hours the plants were infected with leaf pieces heavily infested with mites. Assessment took place after 10 days. The active ingredients were investigated from a concentration of 0.1% downward.

The compounds of Example Nos. 3, 5, 23, 32, 33, 37, 38, 39, 40, 46, 48, 51 and 53 had a virtually full action down to 0.002%. The comparative agent was at least 10 times less effective than the active ingredient according to the invention having the lowest action.

Contact action on ticks (*Ornithodorus moubata*)

The experiment was carried out on young ticks which had sucked blood only once. Paper bags, each containing 5 animals, were dipped for 5 seconds in the aqueous active ingredient formulation. The bags were then suspended. The temperature was kept at 25° to 26° C. The kill rate was determined after 48 hours.

The compounds of Example Nos. 2, 3, 4, 8, 9, 10, 14, 20, 21, 22, 25, 26, 30, 33 and 53 had an absolute action at 0.02, and some at 0.0004 to 0.01%; the comparative agent was still ineffective at 0.1%.

Action on root-knot nematodes (*Meloidogyne incognita*)

Young tomato plants were each planted in 500 g of compost heavily infested with root-knot nematodes. 3 days later, 50 ml of the aqueous active ingredient formulations were applied by spraying in a spray booth. The roots were checked for root-knots after 6 to 8 weeks.

The compounds of Example Nos. 1, 3, 4, 5, 18, 19, 20, 21, 23, 24, 25, 26, 27, 46, 47, 48, 49, 50, 51, 52 and 53 completely inhibited root-knot formation at a concentration of 0.02 to 0.1%; the comparative agent was insufficiently effective at 0.1%.

We claim:

1. A fluoroethoxyphenyl(di)thiophosphate of the formula

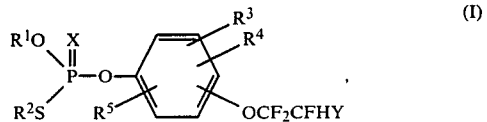

where $R^1$ is ethyl, $R^2$ is alkyl of 3 or 4 carbon atoms, or ethoxyethyl $R^3$, $R^4$ and $R^5$ independently of one another are each hydrogen, chlorine or bromine, X is oxygen or sulfur, and Y is fluorine.

2. A process for combating pests, wherein a fluoroethoxyphenyl(di)thiophosphate of the formula I as claimed in claim 1 is allowed to act on the pests and/or their habitat.

3. A pesticide containing a fluoroethoxyphenyl(di)thiophosphate of the formula I as claimed in claim 1.

4. A pesticide containing inert additives and a fluoroethoxyphenyl(di)thiophosphate of the formula I as claimed in claim 1.

* * * * *